US008834909B2

(12) United States Patent
Rakoczi et al.

(10) Patent No.: US 8,834,909 B2
(45) Date of Patent: Sep. 16, 2014

(54) GRANULE BAITS

(75) Inventors: Ferenc Jozsef Rakoczi, Muttenz (CH);
Jean-Louis Hug, Oltingue/Ferrette (FR)

(73) Assignee: Novartis AG, Basel (CH)

( * ) Notice: Subject to any disclaimer, the term of this patent is extended or adjusted under 35 U.S.C. 154(b) by 2228 days.

(21) Appl. No.: 10/565,520

(22) PCT Filed: Jul. 28, 2004

(86) PCT No.: PCT/EP2004/008465
§ 371 (c)(1),
(2), (4) Date: Jul. 20, 2006

(87) PCT Pub. No.: WO2005/013687
PCT Pub. Date: Feb. 17, 2005

(65) Prior Publication Data
US 2007/0071784 A1    Mar. 29, 2007

(30) Foreign Application Priority Data

Jul. 29, 2003    (EP) .................................... 03017131

(51) Int. Cl.
*A01N 43/88* (2006.01)
*A01N 25/12* (2006.01)
*A01N 25/00* (2006.01)

(52) U.S. Cl.
CPC .......... *A01N 25/006* (2013.01); *Y10S 514/951* (2013.01); *Y10S 514/974* (2013.01)
USPC .......... 424/409; 424/84; 424/410; 514/229.2; 514/777; 514/951; 514/974

(58) Field of Classification Search
None
See application file for complete search history.

(56) References Cited

U.S. PATENT DOCUMENTS

| 4,122,165 | A | 10/1978 | Kinzer et al. |
| 4,205,066 | A | 5/1980 | Hennart et al. |
| 4,855,133 | A * | 8/1989 | Kamei et al. ..................... 424/84 |
| 5,556,631 | A | 9/1996 | Kelley |
| 5,814,652 | A * | 9/1998 | Wu ................................. 514/404 |
| 6,074,634 | A | 6/2000 | Lopez et al. |
| 6,298,597 | B1 | 10/2001 | Koehler et al. |
| 2001/0046986 | A1 * | 11/2001 | Miura et al. .............. 514/211.03 |

FOREIGN PATENT DOCUMENTS

| CN | 1217143 | 6/1999 |
| EP | 0431468 A1 | 6/1991 |
| EP | 0 968 652 | 1/2000 |
| EP | 0968652 | 1/2000 |
| WO | WO9422299 | 10/1994 |
| WO | WO/01/60163 | 8/2001 |

OTHER PUBLICATIONS

STN online, file DRUGU, Ann. No. 1993-28537 (Symecko et al., Drug Dev. Ind. Pharm. (1993), vol. 19, No. 10, pp. 1131-1141), Abstract.*
STN online, file CHEMLIST, Ann. No. 17771 (Hansa Brilliant Yelllow 4GX, C.I. Pigment Yellow, EPA Pesticide Inert Ingredients (May 22, 2002), Abstract.*
Henderson et al., Chemosphere (1998), vol. 36, No. 1, pp. 203-210.*
Schnuch et al., J. Comp. Physiol. A. (1998), vol. 182, pp. 767-775.*
Wiktionary (2013), "granulate" [retrieved on Sep. 27, 2013]. Retrieved from the Internet<URL:http://en.wiktionary.org/wiki/granulate>.*
JP2002275404A (2002), Abstract.*
JP8056542A (1996), Abstract.*
07832C/05 (1980), Abstract.*
JP Associate Memo (2010).*

* cited by examiner

*Primary Examiner* — Abigail Fisher
*Assistant Examiner* — Frank Choi
(74) *Attorney, Agent, or Firm* — Ann R. Pokalsky; Dilworth & Barrese, LLP

(57) ABSTRACT

The invention is directed at a ready-to-use granule bait composition, its preparation and use for the control of house flies inside houses and animal stalls, fodder stores and sanitary installations.

11 Claims, No Drawings

GRANULE BAITS

This application is a National Phase Application under §371 of International Application Number PCT/EP2004/008465 filed on Jul. 28, 2004.

This invention is directed at a ready-to-use granule bait for the control of house flies inside houses and animal stalls, fodder stores and sanitary installations.

House flies are insects which are not only annoying but also harmful to man and animals, in particular because of the pathogenic germs which they carry, such as trypanosomes, rickettsiae, tuberculosis bacillus, leprosy bacillus, cholera vibrio, typhoid bacillus, dysentery bacillus, anthrax-type bacteria, diphtheria bacillus, amoebae, diverse protozoa and eruptive fever virus, and the larvae of which can, furthermore, cause intestinal or cutaneous myases. Therefore, it is well understood that house flies, in particular Diptera of the families Muscidae, Sarcophagidae and Tachinidae, are targeted all over the world.

Pesticidal baits are traditionally formulated with active insect controlling agents, and optionally attractants and tensides onto an inert substrate which is palatable to the targeted pest.

The insecticidal mode of action of the insect-controlling agents is of no importance; the agents may be chitin synthesis inhibitors, growth regulators, juvenile hormones or adulticides. They may also be broad-band insecticides.

The insect controlling agent can be selected from all those which act on the insects by ingestion: the preferred insecticidal agents are selected from the group comprising the esters of N-substituted carbamic acids, organo-phosphorous compounds, nitro-enamines, chlorinated hydrocarbons, pyrethroids, formamidines, borates, phenylpyrazoles and macrocyclic lactones (previously known as avermectins).

Examples of suitable carbamic acid esters are methomyl, 3-methylpyrazol-5-yl dimethylcarbamate, dimetilan, arprocarb, pyrolan, pyramat, dioxacarb, 5,6,7,8-tetrahydronaphth-2-yl N-methylcarbamate, 2-methylquinol-8-yl N-methylcarbamate, o-tert.-butylphenyl N-methylcarbamate, o-tert.butoxyphenyl N-methylcarbamate, o-(prop-2-ynyloxy)-phenyl N-methylcarbamate, o-sec.-butylphenyl N-methylcarbamate, o-sec.-butoxyphenyl N-methylcarbamate, 2,6-dl-tert.-butylphenyl N-methylcarbamate, 2,6-dl-sec.-butylphenyl N-methylcarbamate, 2,6-diisopropylphenyl N-methylcarbamate, 2-tert.-butyl-6-methylphenyl N-methylcarbamate, dimetan and bendiocarb.

Examples of suitable organo-phosphorous compounds are dichlorvos, dibrom, azamethiphos, malathion, diazinon, bromophosethyl, fenthion, fenitrothion, methacriphos, O,O-diethyl O-(3,5,6-trichloropyrid-2-yl)thiophosphate, fenchlorphos, iodofenphos, chlorpyriphos, chlorpyriphosmethyl, propetamphos, S-(2-aza-2-oxo-benzoxazol-3-yl)-methyl O,O-diethyl dithiophosphate and trichlorphon.

Examples of suitable nitro-enamines are imidacloprid and thiamethoxam.

In addition to these examples or in combination with these substances, further insecticidal compounds can be used, such as natural pyrethrins, allethrin, tetramethrin, resmethrin, fenothrin, permethrin, deltamethrin, tralomethrin, fenvalerate, fipronil, rotenone, N,N'-dibutyl-parachlorobenzene-sulfonamide, 1,2,4,5,6,7,8,8-octachloro-3a,4,7,7a-tetrahydro-4:7-methano-indane, gamma-1,2,3,4,5,6-hexachlorocyclohexane, endo-oxo-1,2,3,4,10,10-hexachloro-6,7-epoxy-1,4,4a,5,6,7,8,8a-octahydro-1:4,5:8-dimethanonaphthalene, sodium fluoride and boric acid as well as its salts, and growth regulators such as hydroprene, methoprene, diflubenzuron, lufenuron, noviflumuron, hexaflumuron, triflumuron, teflubenzuron, fenoxycarb, pyriproxifen, kinoprene, cyromazine, buprofezin, pymetrozine and derivatives thereof.

Several substances have been specified for playing the role of lure in insecticidal bait compositions. These are, in particular, muscalure, hexalure, medlure, malt, orange peel oil, vanillin, terpineol, farnesol, geraniol, phenylethanol, hydrolysis products of living cells, formaldehyde, combinations of tertiary amines and carboxylic acids, chlorinated alkenes, extracts from aucuba fruit, aliphatic monoesters of polyols and cis-9-tricosene.

These experiments also showed that the luring effectiveness of these attractants is increased if the bait is coloured yellow. Applicable yellow dyes are water insoluble; typical examples are commercially available yellow dispersion dyes such as Hansa Brillant Yellow 4GX.

Optionally, further adjuvants may be added to the granule composition which function as carriers as well as fly food such as lactose, maltose or glucose, structure-stabilizers (glue) such glucidex or maltodextrin, tensides such as agrimer or any other non-ionogenic dispersants/detergents, bitter constituents such as Bitrex, and filling material such as saccharose, fructofuranose or glucopyranose.

Traditionally, pesticidal granules are formulated on a mineral or cellulose basis such as clay, diatomaceous earth, silica, corn cob, peanut hulls, paper or sugar. These materials tend to be hydrophilic or hygroscopic which not only easily causes the formation of lumps in the package containers once opened, but also induces chemical degradation which reduces their useful life. Therefore, a composition is required that is not only essentially water free but also is hydrophobic enough to endure a long shelf life.

The size of granules should not be too small in order to enable the user to see the treated area and/or to allow their easy removal. On the other hand, for optimal luring effectiveness the granules should not be too large. Experiments have shown that a granule diameter of approximately 3-4 mm is ideal.

These requirements ask for a method of production which ensures a dust free, dry product with a very narrow range of granule size.

The present invention offers the solution to the named problems providing a bait granule that on the one hand has a great luring effect on house flies with a long-lasting efficacy due to its hydrophobicity given by the chemical composition, and has on the other hand a granule size that makes it easily removable due to their good visibility to the user.

The invention thus relates to a granular composition, which can be used as a bait for house flies, comprising an insect controlling agent, a food, a lure, a filling material and optionally a bitter constituent, a luring dye, a structure-stabilizer and a tenside.

Preferably, this bait composition encompasses an insect controlling agent selected from the group comprising the carbamic acid esters methomyl, 3- methylpyrazol -5-yl dimethylcarbamate, dimetilan, arprocarb, pyrolan, pyramat, dioxacarb, 5,6,7,8-tetrahydronaphth-2-yl N-methylcarbamate, 2-methylquinol-8-yl N- methylcarbamate, o-tert.-butylphenyl N-methyl-carbamate, o-tert.butoxyphenyl N-methylcarbamate, o-(prop-2-ynyloxy)-phenyl N-methylcarbamate, o-sec.-butylphenyl N-methylcarbamate, o-sec.-butoxyphenyl N-methylcarbamate, 2,6-di-tert.-butylphenyl N-methylcarbamate, 2,6-dl-sec.-butylphenyl N-methylcarbamate, 2,6-diisopropylphenyl N-methylcarbamate, 2-tert.-butyl-6-methylphenyl N-methyl-carbamate, dimetan and bendiocarb; the nitro-enamines imidacloprid and thiamethoxam; the natural pyrethrins; the pyrethroids allethrin, tetramethrin, resmethrin, fenothrin, permethrin, deltamethrin and tralomethrin; and fipronil;

more preferably, the insect controlling agent is selected from the group comprising imidacloprid and thiamethoxam and fipronil;

most preferably, the insect controlling agent is selected from the group comprising imidacloprid and thiamethoxam;

especially preferred is the insect controlling agent thiamethoxam.

The insect controlling agent is present in the composition in a proportion of about 0.01 percent to about 5 percent, relative to the weight of the composition, preferably of about 0.1 percent to about 2 percent, most preferably of about 0.5 percent to about 1.5 percent.

Preferably, the fly foods are selected from the group comprising lactose, maltose and glucose.

Especially preferred is lactose.

The fly food is present in the composition in a proportion of up to about 25 percent, relative to the weight of the composition, preferably of up to about 10 percent.

Preferably, the lure is selected from the group comprising muscalure, hexalure, medlure, vanillin, terpineol, famesol, geraniol, phenylethanol and cis-9-tricosene.

Especially preferred is cis-9-tricosene.

The lure is present in the composition in a proportion of about 0.001 percent to about 0.5 percent, relative to the weight of the composition, preferably of about 0.01 percent to about 0.2 percent, most preferably of about 0.05 percent to about 0.15 percent.

Preferably, this bait composition also encompasses a bitter constituent as a repellent against any other animals.

Most preferably, the bitter constituent is Bitrex.

The bitter constituent is present in the composition in a proportion of up to about 0.1 percent, relative to the weight of the composition, preferably of up to about 0.01 percent, most preferably of up to about 0.005 percent.

In order to increase the luring efficacy as well as the visibility of the granules the bait composition preferably also encompasses a dye.

Preferred dyes are selected from the group comprising azo dyes.

Especially preferred is Hansa Brillant Yellow 4GX.

The luring dye is present in the composition in a proportion of up to about 1 percent, relative to the weight of the composition, preferably of up to about 0.1 percent.

Preferably, the bait composition also encompasses a structure-stabilizer.

Preferred structure-stabilizers are selected from the group comprising Glucidex or Maltodextrin.

Especially preferred is Glucidex.

The structure-stabilizer is present in the composition in a proportion of up to about 25 percent, relative to the weight of the composition, preferably of up to about 10 percent.

Preferably, the bait composition also encompasses filling material.

Preferred filling materials are selected from the group comprising saccharose, fructofuranose and glucopyranose.

Especially preferred is saccharose.

The filling material is present in the composition in a proportion of up to about 90 percent, relative to the weight of the composition, preferably of up to about 80 percent.

Preferably, the bait composition also encompasses tensides.

An especially preferred tenside is Agrimer.

The tenside is present in the composition in a proportion of up to about 0.1 percent, relative to the weight of the composition, preferably of up to about 0.05 percent.

The invention also relates to the manufacture of the composition of the bait. The preparation of the bait composition is in general effected by the following steps:

a) premixing the constituent material except for the bitter constituent;

b) optionally spraying a solution of the bitter constituent over the premix;

c) spraying water over the final mixture during the granulation process;

d) standardization; and finally e) drying and dry-sieving the granulate.

A further aspect of the invention is the size of the granulate, which is achieved by using an appropriate mesh size of the rasp sieve in the granulation process. A preferred size of the granulate is between about 1 and about 5 mm, more preferably between about 3 and about 4 mm.

A still further aspect of the invention is the fact that by the mentioned preparation steps of the granulate the final product is essentially dust-free in that by the dry-sieving step small particles are filtered out so that the amount of particles smaller than about 0.63 mm is less than about 5%.

The importance of the compositions according to the invention is demonstrated by the following example:

| Ingredients | Amount per 100 kg |
|---|---|
| Thiamethoxam | 1.03 kg |
| Cis-9-Tricosene | 0.17 kg |
| Agrimer AL-10 LC | 0.05 kg |
| Glucidex 2 | 8.50 kg |
| Bitrex | 0.002 kg |
| Hansa Brillant Yellow 4GX | 0.08 kg |
| Powdered Lactose | 10.00 kg |
| Sugar powder (Saccharose) | 80.168 kg |

A typical example of the preparation steps of the bait granulate according to the invention is the following:

EXAMPLE 1

Manufacture of Bait Granulate a) Composition of the Dry Mixture

An amount 40 kg Saccharose is charged into a vertical granulator equipped with a spray nozzle, then 1.03 kg thiamethoxam, 0.05 kg agrimer, 8.5 kg glucidex, 2 g bitrex, 80 g Hansa Brillant Yellow 4GX and 10 kg powdered lactose are added and the mixture intensely homogenized for 5 minutes, whereby the speed of the main mixer is 100 rpm and the chopper speed is 1500 rpm. Finally, another 40.168 kg Saccharose is added and the homogenization continued at unchanged mixer and chopper speed for another 5 minutes. At the end of this first homogenization period, the mixture is sampled to measure the water content by the LOD (Loss on Drying) method. The determined %-LOD (a typical value is 0.6%) will be used for calculation of the required amount of water for the wetting step.

b) Addition of Bitter Constituent on Premix

While the mixing is continued, 170 g tricosene is sprayed over the premix within 2 minutes and the final mixture is homogenized for further 5 minutes. The final mixture is then ready for wetting and granulation.

c) Wetting and Granulation

At the same mixer and chopper speed as before, an amount of 7.8-LOD (in %) kg purified water is sprayed on the final mixture of 100 kg in 15 minutes (approximately 0.48 kg/min) using a spray nozzle with an inner diameter of 1.2 mm in the same vertical granulator at a nozzle pressure of 4-5 bar. Immediately after adding the water the mixer and chopper are stopped and the homogenous wet final mixture is transferred into the wet sieve for standardization.

d) Standardization

The wet final mixture is standardized during 1-2 hours using an appropriate wet sieve. The mesh size of the rasp sieve used is 3 mm. The standardized wet product is immediately transferred into the fluid bed dryer.

e) Drying and Dry-Sieving

The wet standardized product, as it leaves the wet sieve, is continuously transferred into the fluid bed dryer, preheated at 30° C., which is equipped with a conditioned air supply unit and humidity sensor in the exhaust air. The product is dried for 10-20 minutes at 30° C. air inlet temperature and 5000-6000 m$^3$/h air throughput. The dew point of the inlet air is max. 7° C.

After 10-20 minutes of drying, the fluid bed dryer is opened and the product is transferred to the dry sieve standardizer having a square mesh of 5 mm size, where the oversized particles are separated. After the dry standardization, the product is charged again into the fluid bed dryer and dried for approximately 80-100 minutes at 60° C. air inlet temperature and approximately 4000 m$^3$/h air throughput. The air used is conditioned and has a dew point of max. 7° C. Samples are taken every 20 minutes and the LOD of the product is measured. The drying process is completed as soon as the LOD of the product has reached 0.8%. At this point, the exhaust air temperature is at least 54° C. and the rest humidity of the exhaust air has fallen to below 0.145%. The dry product is then sieved to separate particles smaller than 0.63 mm size using a vibration sieve. The dried granules are sampled and prepared for packaging.

What is claimed:

1. A method of preparing a granule bait composition consisting essentially of thiamethoxam wherein the thiamethoxam is present in an amount up to about 5 percent relative to the weight of the granule bait composition; one or more lures wherein the one or more lures are present in an amount up to about 0.5 percent relative to the weight of the granule bait composition and wherein the one or more lures are selected from the group consisting of muscalure, hexalure, medlure, vanillin, terpineol, farnesol, geraniol, phenylethanol, and cis-9-tricosene; one or more foods wherein the one or more foods are present in an amount up to about 25 percent relative to the weight of the granule bait composition and wherein the one or more foods are selected from the group consisting of materials are present in an amount up to about 90 percent relative to the weight of the granule bait composition and wherein the one or more filling materials are selected from the group consisting of saccharose, fructofuranose and glucopyranose, and optionally at least one constituent selected from the group consisting of a bitter constituent, a dye, a structure-stabilizer, and a tenside; wherein the size of the granules making up the granule bait composition is between about 1 mm and about 5 mm; and wherein said granule bait composition is hydrophobic, the method of preparing said granule bait composition comprising:

a) mixing said thiamethoxam, said one or more lures, said one or more foods, said one or more filling materials and optionally said dye, said structure stabilizer or said tenside to form a mixture;

b) optionally spraying a solution of a bitter constituent over said mixture c) granulating said mixture d) spraying water over said mixture during the granulating step;

e) standardizing the granulate;

f) drying the granulate; and g) dry-sieving the granulate.

2. The method of claim 1, wherein due to the dry-sieving step, the amount of granules smaller than about 0.63 mm is less than about 5%.

3. A method of preparing a granule bait composition consisting essentially of thiamethoxam, wherein the thiamethoxam is present in an amount up to about 5 percent relative to the weight of the granule bait composition; one or more lures wherein the one or more lures are present in an amount up to about 0.5 percent relative to the weight of the granule bait composition and wherein the one or more lures are selected from the group consisting of muscalure, hexalure, medlure, vanillin, terpineol, farnesol, geraniol, phenylethanol, and cis-9-tricosene; one or more foods wherein the one or more foods are present in an amount up to about 25 percent relative to the weight of the granule bait composition and wherein the one or more foods are selected from the group consisting of lactose, maltose and glucose; one or more filling materials wherein the one or more filling materials are present in an amount up to about 90 percent relative to the weight of the granule bait composition and wherein the one or more filling materials are selected from the group consisting of saccharose, fructofuranose and glucopyranose; one or more bitter constituents, one or more dyes, and one or more structure-stabilizers, wherein said one or more bitter constituents are a repellent against non-house fly animals, and wherein the size of the granules making up the granule bait composition is between about 1 mm and about 5 mm and wherein the granule bait composition is hydrophobic; the method of preparing comprising:

a) premixing said thiamethoxam, said one or more lures, said one or more foods, said one or more filling materials, said one or more dyes and said one or more structure stabilizers to form a premix;

b) spraying a solution of said one or more bitter constituents over said premix to form a final mixture;

c) granulating said final mixture;

d) spraying water over said final mixture during the granulating step;

e) standardizing the granulate;

f) drying the granulate;

g) and dry-sieving the granulate.

4. The method of claim 3, wherein due to the dry-sieving step, the amount of granules smaller than about 0.63 mm is less than about 5%.

5. A granule bait composition for the control of house flies inside houses and animal stalls, fodder stores, and sanitary installations consisting essentially of:

thiamethoxam, wherein the thiamethoxam is present in an amount up to about 5 percent relative to the weight of the granule bait composition;

one or more lures, wherein the one or more lures are present in an amount up to about 0.5 percent relative to the weight of the granule bait composition and wherein the one or more lures are selected from the group consisting of muscalure, hexalure, medlure, vanillin, terpineol, farnesol, geraniol, phenylethanol, and cis-9-tricosene;

one or more foods, wherein the one or more foods are present in an amount up to about 25 percent relative to the weight of the granule bait composition and wherein the one or more foods are selected from the group consisting of lactose, maltose and glucose; and one or more filling materials, wherein the one or more filling materials are present in an amount up to about 90 percent relative to the weight of the granule bait composition and wherein the one or more filling materials are selected from the group consisting of saccharose, fructofuranose and glucopyranose, and optionally at least one constituent selected from the group consisting of a bitter constituent, a dye, a structure-stabilizer, and a tenside, wherein the size of the granules making up the granule bait composition is between about 1 and 5 mm and the amount of granules smaller than about 0.63 mm is less than about 5% and wherein the granule bait composition is hydrophobic.

6. The granule bait composition according to claim 5, wherein the bitter constituent is present in an amount of up to about 0.1 percent, the dye is present in an amount up to about 1 percent, and the structure-stabilizer is present in an amount of up to about 25 percent, each amount relative to the weight of the granule bait composition.

7. The granule bait composition according to claim 5, wherein the thiamethoxam in the composition is present in an amount of about 0.5 percent to 1.5 percent, the lure is present in an amount of about 0.05 percent to 0.15 percent, the food is present in an amount up to about 10 percent, the filling material is present in an amount up to about 80 percent, the bitter constituent is present in an amount up to about 0.005 percent, the dye is present in an amount up to about 0.1 percent, the structure-stabilizer is present in an amount up to about 10 percent, and the tenside is present in an amount up to about 0.1 percent, each amount relative to the weight of the granule bait composition.

8. The granule bait composition according to claim 5, wherein the lure is cis-9-tricosene, the food is lactose, and the filling material is saccharose.

9. The granule bait composition according to claim 5, wherein the thiamethoxam is present in an amount of about 0.1 percent to 2 percent relative to the weight of the granule bait composition.

10. The granule bait composition according to claim 5, wherein the size of the granules making up the granule bait composition is between about 3 and 4 mm.

11. A method of reducing the number of house flies in a location comprising spreading the granule bait composition of claim 5 around said location.

* * * * *